United States Patent [19]

Williams

[11] Patent Number: Plant 6,199

[45] Date of Patent: Jun. 14, 1988

[54] ROSE PLANT NAMED MINWCO

[76] Inventor: Ernest D. Williams, 1510 Lebanon Ave., Dallas, Tex. 75208

[21] Appl. No.: 857,480

[22] Filed: Apr. 30, 1986

[51] Int. Cl.[4] ..... A01H 5/00

[52] U.S. Cl. ..... Plt./9

[58] Field of Search ..... Plt./9

*Primary Examiner*—Robert E. Bagwill

[57] ABSTRACT

This invention relates to a new and distinct variety of miniature rose plant primarily identified by the light pink color and by the long pointed buds of exhibition form.

1 Drawing Sheet

1

The present invention relates to a new and distinct variety of hardy, dwarf, bush type rose plant of the miniature class; the variety being primarily characterized, as to novelty, by the glowing light pink color and by the long pointed buds of exhibition form.

The variety is further characterized by:

An abundance of bloom, with flowers usually borne singly, but also several to the stem in loose clusters.

Some fragrance.

A plant which is vigorous, of rounded, upright shape with small semi-glossy to matt foliage with pointed leaflets; the buds and flowers being similar in form and size to Dreamglo (miniature—U.S. Plant Pat. No. 4,579).

The plant, which has a normal height of 12–14 inches (30 cm) or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Tom Brown (Floribunda—not patented) as the seed parent and Black Jack (miniature—U.S. Plant Pat. No. 5,671) as the pollen parent.

Subsequent to origination of the variety, I successfully asexually reproduced it at my nursery, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

Variety identification: Minwco (Commercial synonym: Beautyglo).

Flowers borne: Singly and several together 3 to 5) on wirey stems.

Quantity of bloom: Abundant both outside and in greenhouse.

2

Bud:

*Peduncle.*—Medium to long; slender but sturdy; erect; medium green, sometimes tinted bronze (outdoors); with no prickles and few or no short hairs.

*Before calyx breaks.*—Size — small.

*Form.*—Long; pointed, with several foliaceous apendages extending beyond the tip of the bud equal to one-half or less of its length.

*Color.*—Medium to dark green, occasionally tinted with bronze (outdoors).

*As calyx breaks.*—Color — pink. Opening: opens well in all weather.

Bloom:

*Size when fully open.*—Small, averaging about 35 mm (1½").

*Petalage.*—Double — averaging about 25–30 petals arranged regularly plus, sometimes, several small petaloids.

*Form.*—High centered with petals rolled loosely outward and downward. Open flowers usually show stamens.

Petals: Fairly thick; satiny on inside and on outside surface.

*Shape.*—Outside petals, broad lanceolate (nearly round), without acute tip; intermediate — broad lanceolate; inside — lanceolate.

Color: Newly opened flower from plant grown at Dallas, Tex., (May, 1985).

*Outside petal.*—Outside surface — near Carmine Rose 621/2 with both lighter and darker areas and blending into a small yellowish area at base. Inside surface — near Carmine Rose 621/2 (also with both lighter and darker areas) and blending into a small yellowish area at base.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — light pink. Three days open — color, light pink. Behavior — opens well in all weather. Spent petals drop off. Flower longevity (May, 1985) — plant in pot 4–6 days or longer. Cut flowers at living room temperature, 4–5 days or longer.

Reproductive organs:

*Stamens.*—Several.

*Anthers.*—Yellow.

*Pollen.*—Some.

*Pistils.*—Average number.

*Styles.*—Varying length, greenish, bunched.

*Ovaries.*—All enclosed in calyx.

*Sepals.*—Permanent; spear shaped; recurved.

Foliage:

*Leaves.*—Compound of five (sometimes three or seven) leaflets; medium small; leathery; semi-glossy to matt.

*Leaflets.*—Shape: broad lanceolate; apex acute; base rounded, sometimes acute.

*Color.*—Medium to dark green; new growth — normal (medium) green (sometimes tinted reddish).

*Rachis.*—Medium strength; upper side may have several tiny short hairs; grooved; underside may have several thorns (2–3).

*Stipules.*—Medium to short length; medium width; medium length narrow points which turn out usually at about 45 degrees.

Growth:

*Habit.*—Dwarf; bushy; upright; much branched.

*Growth.*—Free; vigorous; internodes short.

*Canes.*—Medium; slender; sturdy.

*Main stems.*—Color: medium green. Thorns — average to less than average. Prickles — none. Hairs — none.

*Branches.*—Color: medium green. thorns: few; slender; prickles — none. Hairs — none.

The miniature rose plant and its flowers as herein described may vary in slight detail due to climatic, soil and cultural conditions under which the variety may be grown; the present description being of the variety as grown in Dallas, Tex.

The following is claimed:

1. A new and distinct variety of miniature rose plant of hardy, dwarf, bushy, upright, much branched habit, substantially as illustrated and described, characterized by buds and flowers of exhibition form in a light pink color, and further characterized by a plant of compact well rounded growth habit; vigorous, with the main stems and shoots being of average, or less, thorniness, the plant being easy to propagate from cuttings, with an abundance of small semi-glossy to matt foliage and an abundance of flowers borne singly or several to the stem in loose clusters.

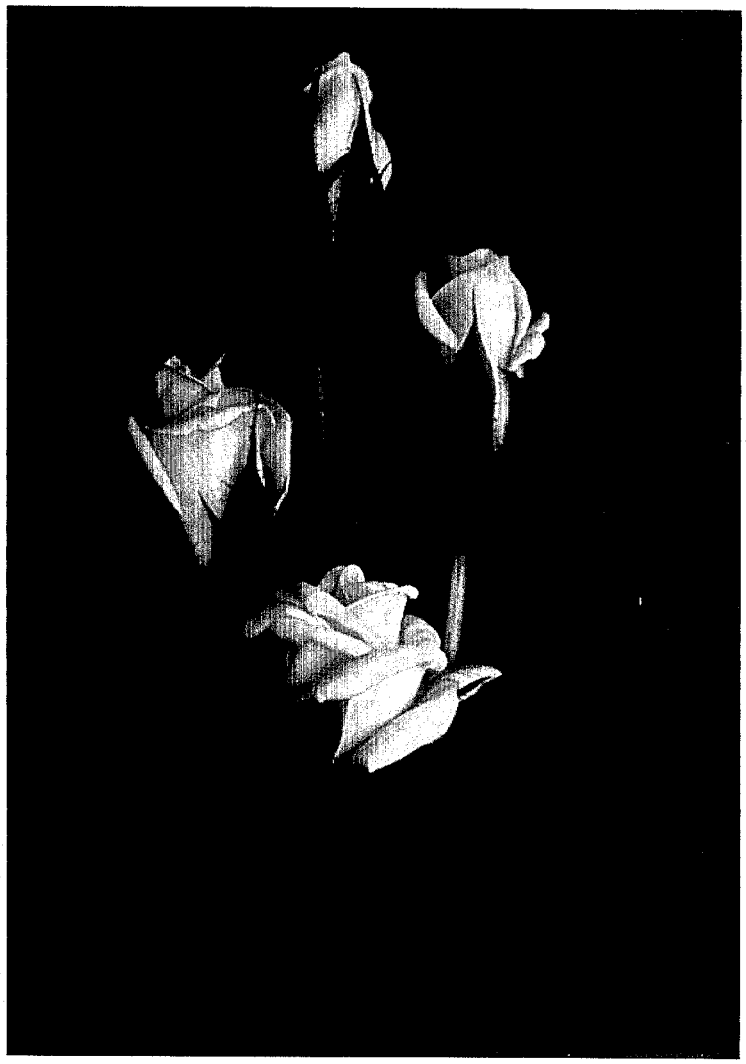

* * * * *